United States Patent
Grube et al.

(10) Patent No.: US 9,895,075 B2
(45) Date of Patent: Feb. 20, 2018

(54) DIAGNOSTIC REPRESENTATION AND INTERPRETATION OF ECG LEADS ON A DIGITAL DISPLAY

(71) Applicant: KONINKLIJKE PHILIPS N.V., Eindhoven (NL)

(72) Inventors: William Douglas Grube, Windham, NH (US); Richard E. Gregg, Westford, MA (US); Patrick Guiney, Concord, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/437,299

(22) PCT Filed: Oct. 21, 2013

(86) PCT No.: PCT/IB2013/059497
§ 371 (c)(1),
(2) Date: Apr. 21, 2015

(87) PCT Pub. No.: WO2014/064595
PCT Pub. Date: May 1, 2014

(65) Prior Publication Data
US 2015/0282726 A1 Oct. 8, 2015

Related U.S. Application Data

(60) Provisional application No. 61/718,905, filed on Oct. 26, 2012.

(51) Int. Cl.
*A61B 5/04* (2006.01)
*A61B 5/044* (2006.01)
(Continued)

(52) U.S. Cl.
CPC ............ *A61B 5/044* (2013.01); *A61B 5/0408* (2013.01); *A61B 5/04012* (2013.01);
(Continued)

(58) Field of Classification Search
CPC . A61B 5/04012; A61B 5/0402; A61B 5/0408; A61B 5/0432; A61B 5/044;
(Continued)

(56) References Cited

U.S. PATENT DOCUMENTS 4,989,610 A 2/1991 Patton et al.
6,312,381 B1 * 11/2001 Knell ................. A61B 8/06
600/437
(Continued)

FOREIGN PATENT DOCUMENTS

EP 0316800 A2 5/1989
EP 1110503 A2 6/2001

*Primary Examiner* — Lindsey G Wehrheim (57) ABSTRACT

A system for electrocardiogram (ECG) interpretation includes a processor and memory coupled to the processor. A rendering module is stored in the memory and is configured to receive input from an ECG and correlate interpretation statements with ECG measurements responsible for the interpretation statements in the ECG. An interface is configured to permit user selection of at least one interpretation statement in a display, the display being configured to render visual indications of the ECG measurements on digitally rendered waveforms of the ECG.

27 Claims, 6 Drawing Sheets

(51) Int. Cl.
*A61B 5/0452* (2006.01)
*G06F 19/00* (2018.01)
*A61B 5/0408* (2006.01)
*A61B 5/0432* (2006.01)
*A61B 5/00* (2006.01)
*G06F 3/0484* (2013.01)
*A61B 5/0402* (2006.01)

(52) U.S. Cl.
CPC .......... *A61B 5/0432* (2013.01); *A61B 5/0452* (2013.01); *A61B 5/4836* (2013.01); *A61B 5/7246* (2013.01); *A61B 5/748* (2013.01); *G06F 3/04842* (2013.01); *G06F 19/345* (2013.01); *G06F 19/3487* (2013.01); *A61B 5/0402* (2013.01)

(58) Field of Classification Search
CPC ... A61B 5/0452; A61B 5/4836; A61B 5/7246; A61B 5/748; G06F 19/345; G06F 19/3487; G06F 3/04842
See application file for complete search history.

(56) References Cited

U.S. PATENT DOCUMENTS

| | | |
|---|---|---|
| 6,463,320 B1 | 10/2002 | Xue et al. |
| 8,280,749 B2 | 10/2012 | Hsieh et al. |
| 2002/0069215 A1* | 6/2002 | Orbanes ................ G06F 3/0346 715/233 |
| 2003/0176802 A1* | 9/2003 | Galen .................... A61B 5/044 600/523 |
| 2004/0260192 A1 | 12/2004 | Yamamoto |
| 2009/0228298 A1 | 9/2009 | Xue |
| 2012/0182301 A1 | 7/2012 | Wenholz et al. |
| 2015/0282728 A1 | 10/2015 | Grube et al. |

* cited by examiner

DIAGNOSTIC REPRESENTATION AND INTERPRETATION OF ECG LEADS ON A DIGITAL DISPLAY

RELATED APPLICATION DATA

This application is a national stage application under 35 U.S.C. § 371 of International Application No. PCT/IB2013/059497 filed on Oct. 21, 2013 and published in the English language on May 1, 2014 as International Publication No. WO 2014/064595 A1, which claims priority to U.S. Application No. 61/718,905 filed on Oct. 26, 2012, the entire disclosures of which are incorporated herein by reference.

BACKGROUND

Technical Field

This disclosure relates to medical instruments and more particularly to electrocardiograph (ECG) equipment and display/interpretation of ECG signals.

Description of the Related Art

An electrocardiograph (e.g., a 12-lead diagnostic device) generates a report called an electrocardiogram. An electrocardiograph (ECG) signal is a 10 second snapshot of the electrical activity of the heart. The electrocardiogram or ECG report includes patient demographics and ECG interpretation in text format on top of a piece of paper with the ECG signal trace shown on a bottom portion of the paper. The orientation of the paper is generally landscape.

An interpretation of the ECG report through an analysis of the ECG measurements is provided. The interpretation is a set of statements, one statement per line, which describes clinical conditions that can be detected from ECG measurements. Under this interpretation, a severity (e.g., "normal" or "abnormal") is included, which is an overall summary of the ECG interpretation.

With today's cardiographs, monitors and defibrillators, a diagnostic representation of ECG leads is only known to be available on a printed strip of paper from a strip chart printer. An ECG lead is the signal measured between two ECG electrodes or one electrode and a combination of electrodes making up the voltage reference for the first electrode. These devices do not have the ability to display ECG leads with the appropriate resolution and with a grid for calibrated time and amplitude measurements for diagnostic use. The use of strip chart printers in the field is not ideal because the printed strips can be easily lost or damaged, and the printers do not always offer reliable performance. The size of the print area on the printed strips is also limited. For users, especially those who are not experts, the reasons for each element of the ECG interpretation may not be clear from the printed strips of the 12-lead ECG.

SUMMARY

In accordance with the present principles, a system for electrocardiogram (ECG) interpretation includes a processor and memory coupled to the processor. A rendering module is stored in the memory and is configured to receive input from an ECG and correlate interpretation statements with ECG measurements responsible for the interpretation statements in the ECG. An interface is configured to permit user selection of at least one interpretation statement in a display, the display being configured to render visual indications of the ECG measurements on digitally rendered waveforms of the ECG.

Another system for interpreting an electrocardiogram (ECG) includes an interpretation module configured to interpret an ECG to provide interpretation statements based on measurements of ECG waveforms, and a rendering module configured in non-transitory storage media to associate the interpretation statements with corresponding measurements on the ECG waveforms. A display is configured to display the interpretation statements and the ECG waveforms. A selection device is configured to select an interpretation statement for explanation, such that the rendering module renders the corresponding measurements associated with the interpretation statement on the ECG waveform to indicate reference locations and provide labels to explain the interpretation statement.

A method for interpreting an electrocardiogram (ECG) includes interpreting an ECG to provide interpretation statements based on measurements of ECG waveforms; associating the interpretation statements with corresponding measurements on the ECG waveforms; displaying the interpretation statements and the ECG waveforms; selecting an interpretation statement to permit explanation; and rendering the corresponding measurements associated with the interpretation statement on the ECG waveform to indicate reference locations and provide labels to explain the interpretation statement.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, medical systems, devices and methods are provided for electrocardiograph (ECG) monitoring and interpretation, including but not limited to multiple-lead ECG, Q-waves, ST elevation and ST depression, etc., as may be implemented and used within a patient monitor, defibrillator or other device, for example. In other embodiments, ECG leads are digitally displayed with a set or variable resolution, and a grid is displayed with at least calibrated time and amplitude measurements on an electronic display of a monitor/defibrillator to enable diagnosis of a patient's condition, including but not limited to ECG resolution, diagnostic bandwidth, 12-lead ECG, as may be implemented and used within an electrocardiograph, patient monitor and/or defibrillator, for example.

In particularly useful embodiments, the present principles provide for digitally rendered ECG signal waveforms. These waveforms may be fitted or scaled to a given display window. In one useful embodiment, the displayed waveforms are coded to permit self-identification of features when a cursor or other pointing device selects or hovers over the waveform in the digital display. The self-identification feature renders a text box to identify a portion of portions of the waveform being selected or hovered over. In another embodiment, a text description of a portion of the waveform may be entered, which causes the described feature to be highlighted in the digital rendering of the waveform. Other embodiments and variations are also contemplated as will be described herein.

In a particularly useful embodiment, portions of the ECG waveforms that contribute to an interpretation statement are digitally highlighted on the waveform to provide a better explanation of the interpretation statement. The digitally highlighted portions may include boxes, shapes, labels, text, lines, etc. indicating portions of the ECG waveform that contributed to the interpretation statement selected by a user.

It should be understood that the present invention will be described in terms of medical instruments and, in particular, electrocardiographs, defibrillators and/or monitors; however, the teachings of the present invention are much broader and are applicable to any device for monitoring or viewing digitally rendered waveforms whether the waveforms are real-time or snapshots. In some embodiments, the present principles are employed in tracking or analyzing complex biological or mechanical systems. In particular, the present principles are applicable to internal tracking procedures of biological systems, procedures in all areas of the body such as the lungs, heart, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
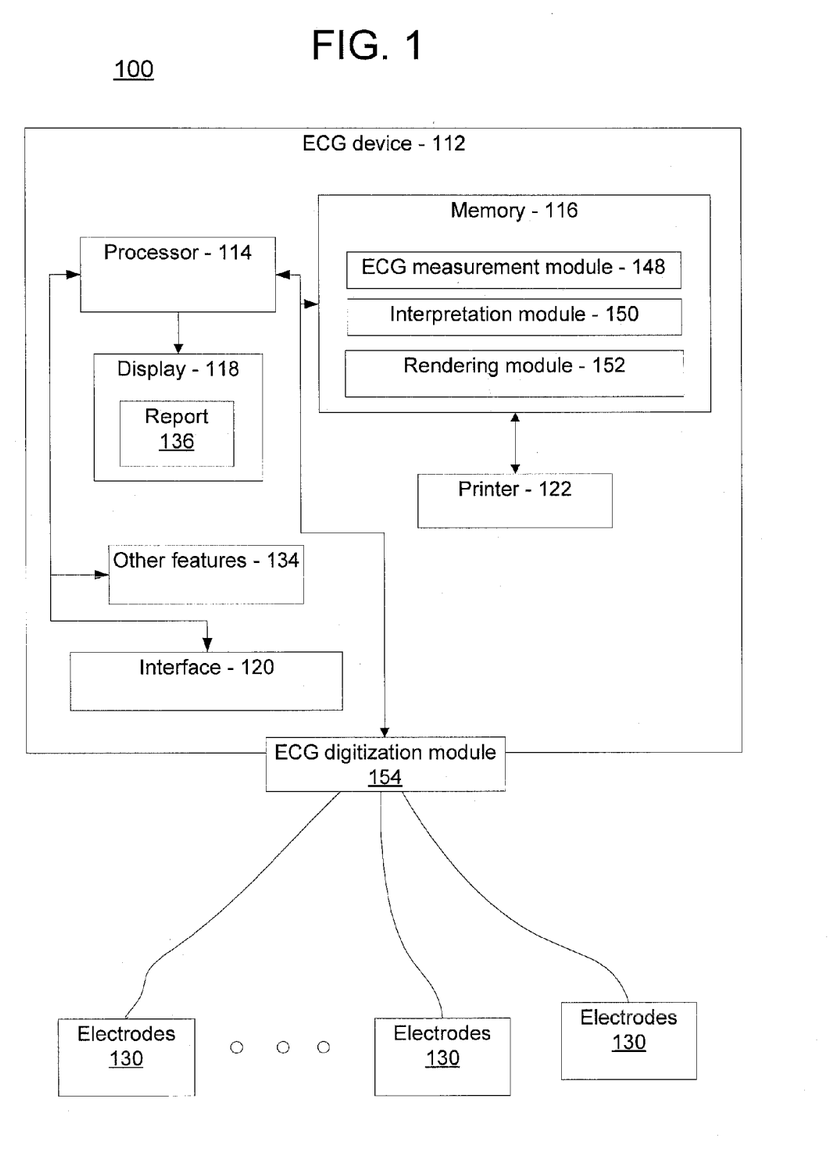
FIG. 1 is a block/flow diagram showing a system for producing and interpreting electrocardiograms (ECGs) in accordance with the present principles.

Referring now to the drawings in which like numerals represent the same or similar elements and initially to FIG. 1, an ECG system 100 is illustratively shown in accordance with one embodiment. System 100 may include an ECG device or workstation 112 from which ECG measurements or tests are taken and supervised, for example, in a cardiograph, patient monitor or defibrillator. Workstation 112 preferably includes one or more processors 114 and memory 116 for storing programs and applications. Memory 116 may store an electrocardiogram rendering system or module 152, which includes or works with one or more modules that permit a user to view, analyze and edit an ECG report 136. The report 136 is preferably digitally rendered on a display 118 using the rendering system 152. The rendering module 152 is coupled to an interface 120 configured to permit input of data to mark, label, highlight or otherwise designate portions of ECG leads (e.g., an output waveform) as will be described. An ECG digitization module 154 digitizes the outputs from electrodes 130 for use by the rendering system 152, e.g., analog to digital conversion. The electrodes 130 connect to the digitization module 154. An ECG measurement module 148 employs the digitized outputs from the digitization module 154 to perform measurements on the measurement data collected from a patient or other system. An interpretation module 150 uses the measurement information from the measurement module 148 to issue interpretation statements.

According to exemplary embodiments, a display resolution and grid can enable a diagnostic representation of ECG leads on an electronic display 118 of the monitor/defibrillator 112. For example, a monitor/defibrillator display 118 can have sufficient resolution, measured in, e.g., dots per inch (DPI), after zooming in on the waveform, to provide diagnostic resolution as specified in applicable international ECG standards. The display 118 may be part of a main housing of the system 112, may be part of an associated tablet or PC coupled to the output, or be part of an associated handheld display unit or other display device mechanism, located locally or remotely, and connected directly or indirectly via wires or wirelessly, or through the internet, for example. The system 112, e.g., monitor, defibrillator, ECG device, etc., can display ECG lead tracings overlaid on a grid with the appropriate time and amplitude scales. The grid can be displayed for both real-time ECG lead waves and also for acquired (e.g., 12 or 16-lead) ECG segments that are reviewed on the display 118.

Exemplary applications for system 100 may include, but are not limited to: e.g., Emergency Medical Services (EMS); Advanced Life Support (ALS) care; Hospital ALS care; Aeromedical transport; ST Elevation Myocardial Infarction (STEMI) programs; American Heart Association "door-to-balloon" initiatives; 12-lead ECG analysis and/or 12+lead (16, 18 or more) ECG analysis, etc. Moreover, as one having ordinary skill in the art will appreciate in view of the teachings provided herein, multiple combinations of displays in accordance with exemplary embodiments described herein are possible, providing for, e.g., individual users to have their own unique display and/or be presented with the same information of other users, regardless of the movement and location of a user. Additionally, it is possible for a user to initially select and change at any time specific information being displayed or highlighted to them by, e.g., selecting from predefined templates, selecting specific informational fields, selecting the display of another particular user, etc.

The ECG device 112 includes the display 118 for viewing the report 136 and may include or show other data or provide an interface (e.g., a touch screen, a mouse or trackball controlled cursor, etc.) for controlling or managing the ECG device 112. Display 118 may also permit a user to interact with the ECG device 112 and its components and functions, or any other element within the system 100. This is further facilitated by the interface 120 which may include a keyboard, mouse, a joystick, a haptic device, or any other peripheral or control to permit user feedback from and interaction with the ECG device 112. The ECG device 112 may also include a printer 122 for outputting the report 136 or other pertinent information, if needed. The ECG device 112 may include other features and capabilities 134, such as alarms, power connections, other software features, etc.

The ECG device 112 may include a plurality of electrodes 130 to be connected to a patient for taking measurements. The number and type of electrodes 130 may vary depending on the application, device and testing protocol. In one example, the Philips® 12/16-lead DXL and earlier versions of the Philips® 12-lead ECG may be employed.

In one example, the Philips® 12/16-lead DXL algorithm and earlier versions of the Philips® 12-lead ECG algorithm (e.g., interpretation module 150) provide interpretive statements describing the ECG rhythm and any abnormalities found in the 10 second resting ECG. The statements have two parts, a description of the condition on the left, and a list of ECG criteria which are met for this condition, or the reason why the statement appears. Other formats are also contemplated. These reasons help the clinician reviewing and possibly correcting the ECG report to understand why the automated algorithm (e.g., interpretation module 150) provided the statement. In some instances, the statements and their basis may not be easily understood or the features being considered or analyzed may not be readily identifiable in the ECG waveform.

Understanding the reasons why the statement appears can help the clinician to either keep or delete that statement while editing. If the ECG criteria in the reasons are not met, and the clinician suspects that the statement is not correct, the clinician can factor the additional information into their decision making or even cross out or remove the statement. In addition, if the ECG criteria are met, the clinician can feel confident that the statement belongs.

To extend the "reasons" part of the interpretation one step further, the abnormalities in the waveform itself can be highlighted in accordance with the present principles. This feature can be useful for both the expert and novice ECG reader. For both, it can help in understanding the ECG interpretation quickly at a glance rather than reading the interpretation and then scanning that part of the waveform. For clinicians who rely on their own read of the ECG more than on the interpretive statements generated by the ECG algorithm (e.g., interpretation module 150), this feature can help by directing their attention to characteristics of interest.

According to exemplary embodiments, visual highlighting of features of the ECG waveforms (and other waveforms) that exceed accepted clinical thresholds may be performed and are, therefore, clinically significant in the interpretation of the waves and diagnosis of a patient condition. Visual highlighting can be evident on ECG waves that are presented, e.g., on the electronic display 118 of a cardiograph, patient monitor, or monitor/defibrillator as well as in electronic reports 136 and physical printouts generated by these devices.

For example, the following are exemplary ways that a user can interact with digitally rendered waveforms. In one example, abnormalities based on ECG criteria and/or abnormalities called out in the interpretation can be emphasized by use of one or more (e.g., in a particular combination or configuration) of the following: different color (or shade) and thickness of the waveform interval, segment or deflection; highlighting behind the waveform interval, segment or deflection, circle, square or some other shape around the waveform; and/or arrow pointing to the waveform. Other visual or audio features are also contemplated. In one embodiment, a hovering cursor over a highlighted ECG feature can be employed to emphasize the applicable part of the ECG interpretation. The hovering cursor over the ECG interpretation may also emphasize the applicable highlighted part or parts of the ECG waveform. Hovering over the highlighted ECG feature can display the interpretation statement in a tool-tip type of pop-up or message box.

In still other embodiments, abnormal sections of the waveform may be named or labeled so that the waveform name or label in the interpretation can be recognized in the waveform. Critical measurements, e.g., such as ST elevation, may be displayed next to the highlighted area or in a designated region. Moving a cursor or "hovering" can be accomplished with a touch screen, mouse, trackball, etc.

Figure 2:
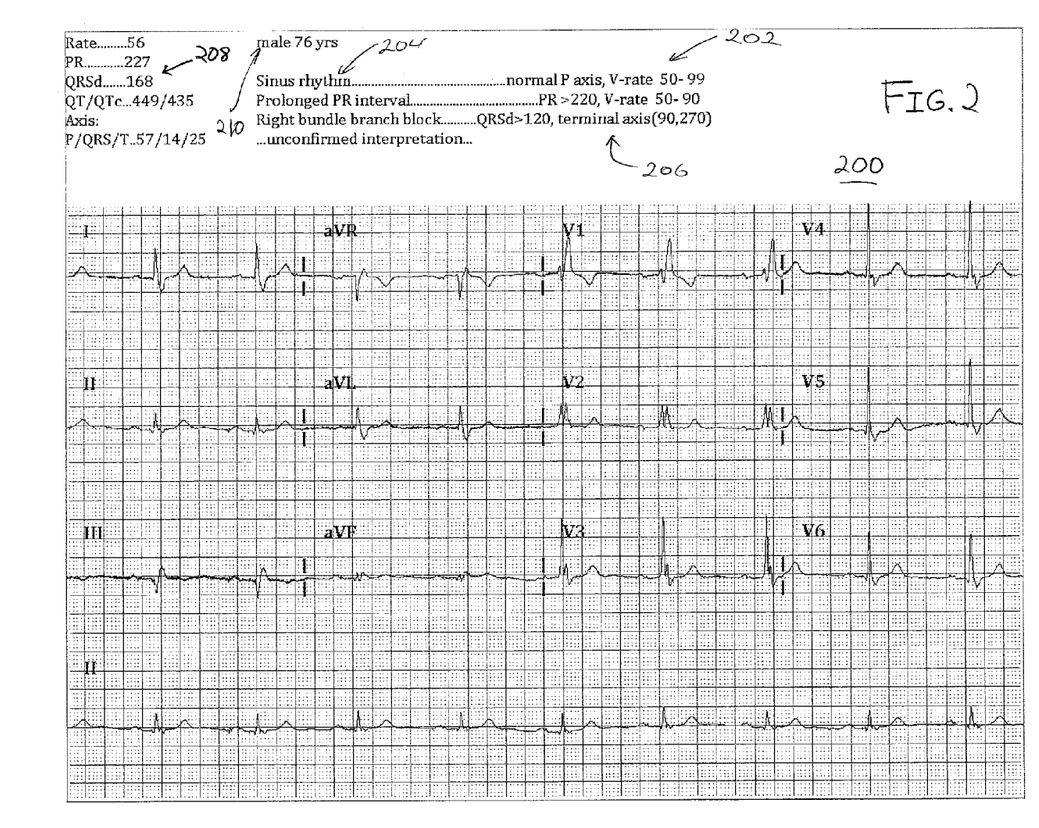
FIG. 2 is a 12-lead ECG report showing waveforms and interpretation statements in a single view.
Figure 3:
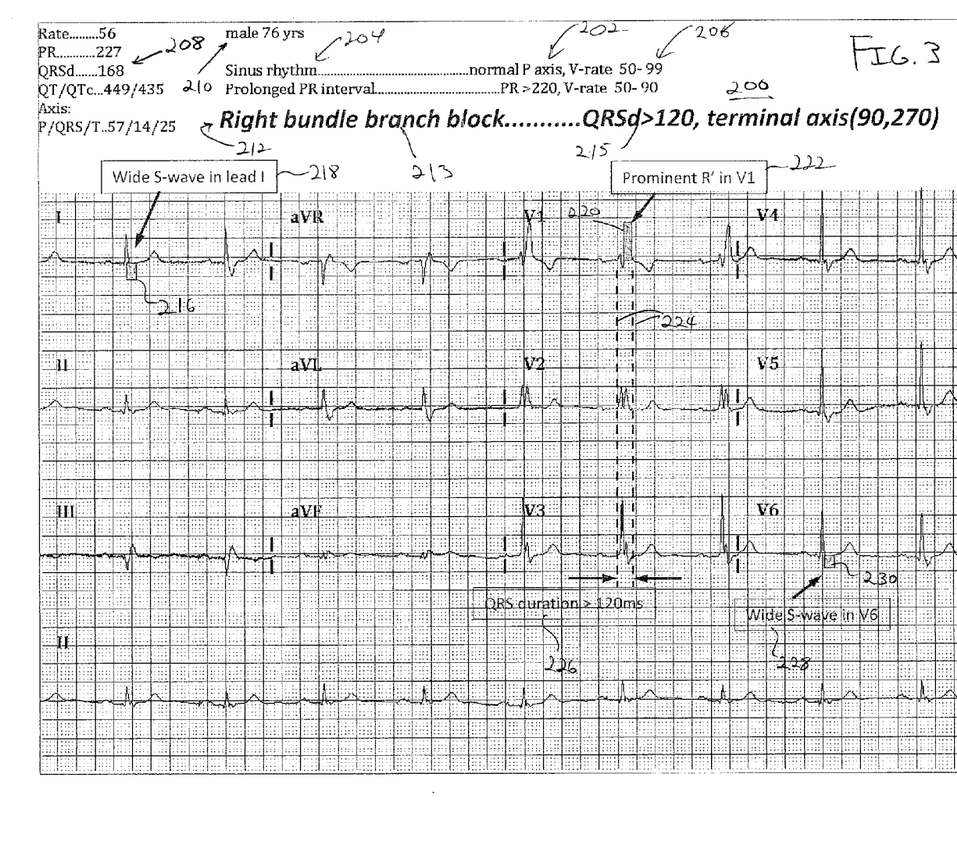
FIG. 3 is a 12-lead ECG report showing a selected interpretation statement and associated annotations on the waveforms digitally rendered in accordance with the present principles.
Figure 4:
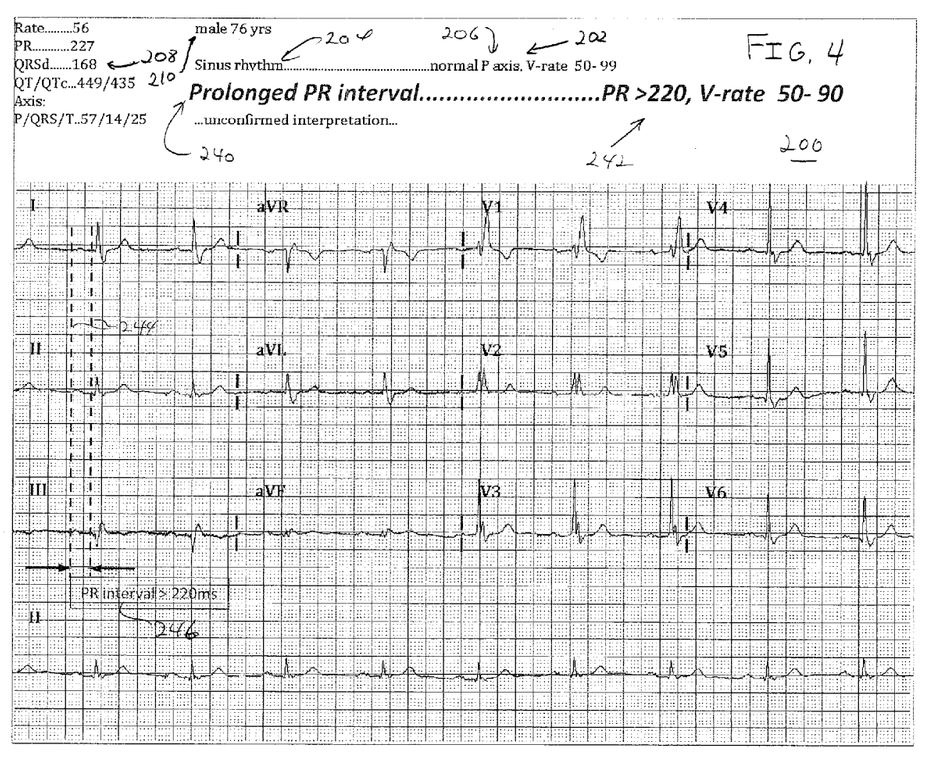
FIG. 4 is an ECG report showing another selected interpretation statement and associated annotations on the waveforms digitally rendered in accordance with the present principles.

FIGS. 2-4 show examples of interpretive statements being highlighted in text to highlight corresponding features in the ECG waveforms in example reports. FIG. 2 is a 12-lead ECG report. FIG. 3 and FIG. 4 show what happens when the user selects a statement from the interpretation. It should be noted that the reverse action may be employed as well. For example, a portion of the waveform may be selected and the applicable interpretive statement may be highlighted.

Referring to FIG. 2, an example 12-lead ECG report 200 is shown in accordance with an exemplary embodiment. The report 200 includes interpretative statements 202, which have two parts, a description 204 of the condition on the left, and a list 206 of ECG criteria which are met for this condition, or the reason why the statement appears. These reasons 206 help the clinician reviewing and possibly correcting the ECG report to understand why the automated algorithm provided the statement. In some instances, the statements and their basis may not be easily understood or the features being considered or analyzed may not be readily identifiable in ECG waveforms I, II, III, . . . V6 provided therein. Other measured data 208 or entered data 210 may also be provided.

Referring to FIG. 3, in accordance with one embodiment, an interpretation statement 212 is selected by using a cursor guided by a mouse, arrow keys or selected by touch screen, etc. In this example, the interpretation statement 212 includes right bundle branch block (RBBB). The interpretation statement 212 becomes highlighted (e.g., changed color, font size, text features. etc., and the applicable measurements appear referenced to the ECG waveform (I, II, III, etc.). For example, the list 206 includes a QRS duration 215 over 120 ms. As a result of highlighting/selecting the interpretative statement 212, an applicable measurement 224 shows the bounds of the QRS wave portion and a corresponding label 226. Other pertinent measurements include a wide S-wave in lead I labeled 218 with a corresponding box 216, and a wide S-wave in V6 labeled 228 with a corresponding box 230. A prominent R' in V1 is also highlighted with a box 220 and a label 222. In this way, a user can instantly see the features of the lead waveforms that contribute to a particle interpretative statement (e.g., 212 in this case).

Referring to FIG. 4, in accordance with another embodiment, an interpretation statement 240 is selected by using a cursor guided by a mouse, arrow keys or selected by touch screen, etc. In this example, the interpretation statement 240 includes prolonged PR interval. The interpretation statement 240 becomes highlighted (e.g., changed color, font size, text features. etc., and the applicable measurements appear referenced to the ECG waveform (I, II, III, etc.). For example, the ECG criteria list includes a PR duration 242 over 220 ms. As a result of highlighting/selecting the interpretative statement 240, an applicable measurement 244 shows the bounds of the PR interval in the wave portion and a corresponding label 246.

In accordance with the present principles, boxes are implemented in the waveform areas to show pertinent portions of the waveform; however, other shapes and visual mechanisms may be employed (e.g., circles, dotted lines, textures or colors, etc.). These boxes correspond with the highlighted or italicized text in the interpretation statement(s); however, this is just one example, to show the correspondence between ECG waveform and textual interpretation in accordance with the present principles. Exemplary applications can include, but are not limited to: e.g., resting 12-lead ECG interpretation; stress test ECG interpretation; monitoring waveform interpretation, including ECG and other waveforms such as capnograms, alarm strip interpretation, including marking features for rhythm interpretation, etc. Moreover, as one having ordinary skill in the art will appreciate in view of the teachings provided herein, multiple combinations of displays in accordance with exemplary embodiments described herein are possible, providing for, e.g., individual users to have their own unique display and/or be presented with the same information of other users, regardless of the movement and location of a user. Additionally, it is possible for a user to initially select and change at any time what specific information is displayed or highlighted to them by, e.g., selecting from predefined templates, selecting specific informational fields, selecting the display of another particular user, etc.

Figure 5:
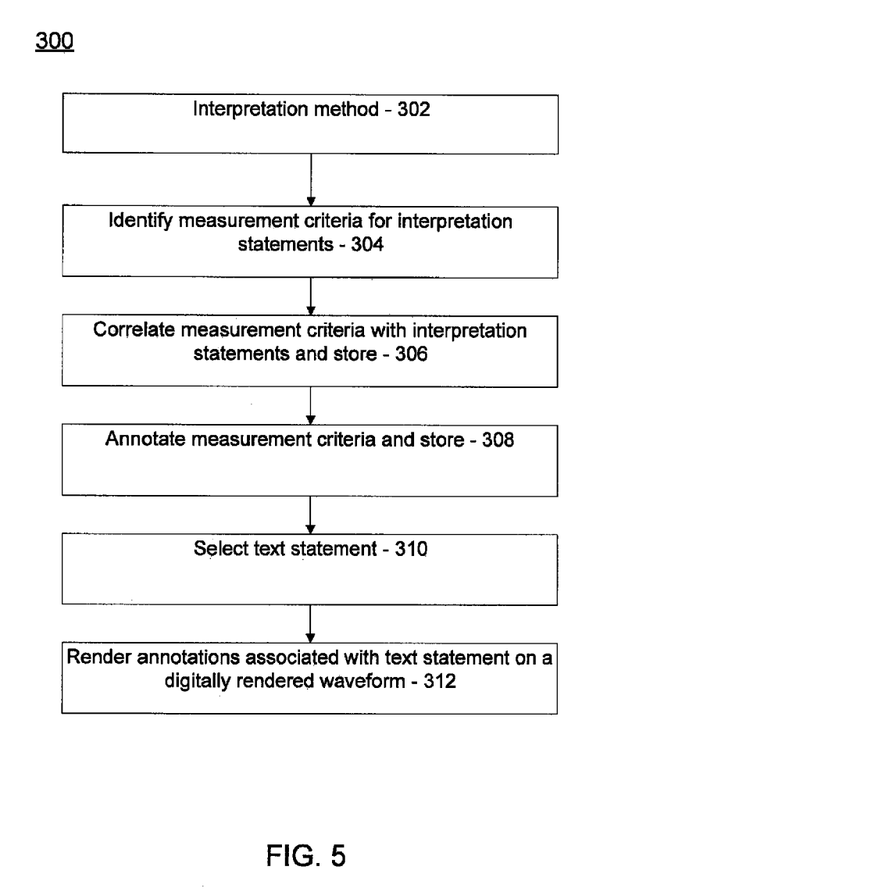
FIG. 5 is a block/flow diagram showing a system/method for producing and interpreting ECGs in accordance with one illustrative embodiment.

Referring to FIG. 5, an ECG rendering system/method 300 (e.g., module 152 of FIG. 1) is shown, which includes one or more modules that permit a user to view, analyze and edit an ECG report. In block 302, an ECG is run and interpreted automatically using an interpretation algorithm or method known in the art. The waveform shapes are identified. In block 304, for each textual statement in the ECG interpretation (interpretation statements output in block 302), specific positive ECG criteria are identified in the waveforms and stored for both measured values and threshold value(s).

In block 306, each measurement involved in determining the text statement, i.e., the measured value, the threshold, and the location of the measurement relative to the ECG waveform, etc. are correlated and stored. When the particular text statement is selected by the user, the stored values are used to draw reference lines or boxes along with labels to indicate the ECG criteria which triggered the interpretation. In block 308, the measurements/measurement criteria involved in an interpretative statement are annotated on the signal with dotted lines, boxes, labels, etc. to show the amplitude, duration or other measurement. These annotations are stored for later rendering.

In block 310, one text statement is selected at a time so that the ECG measurements, thresholds and measurement locations are not confused between different text statements. Selection may be provided using known methods, such as point and click, touch screen, etc. In block 312, the annotations associated with the text statement (interpretation statements) are rendered digitally or as a digital image or digital rendering on the waveforms.

Figure 6:
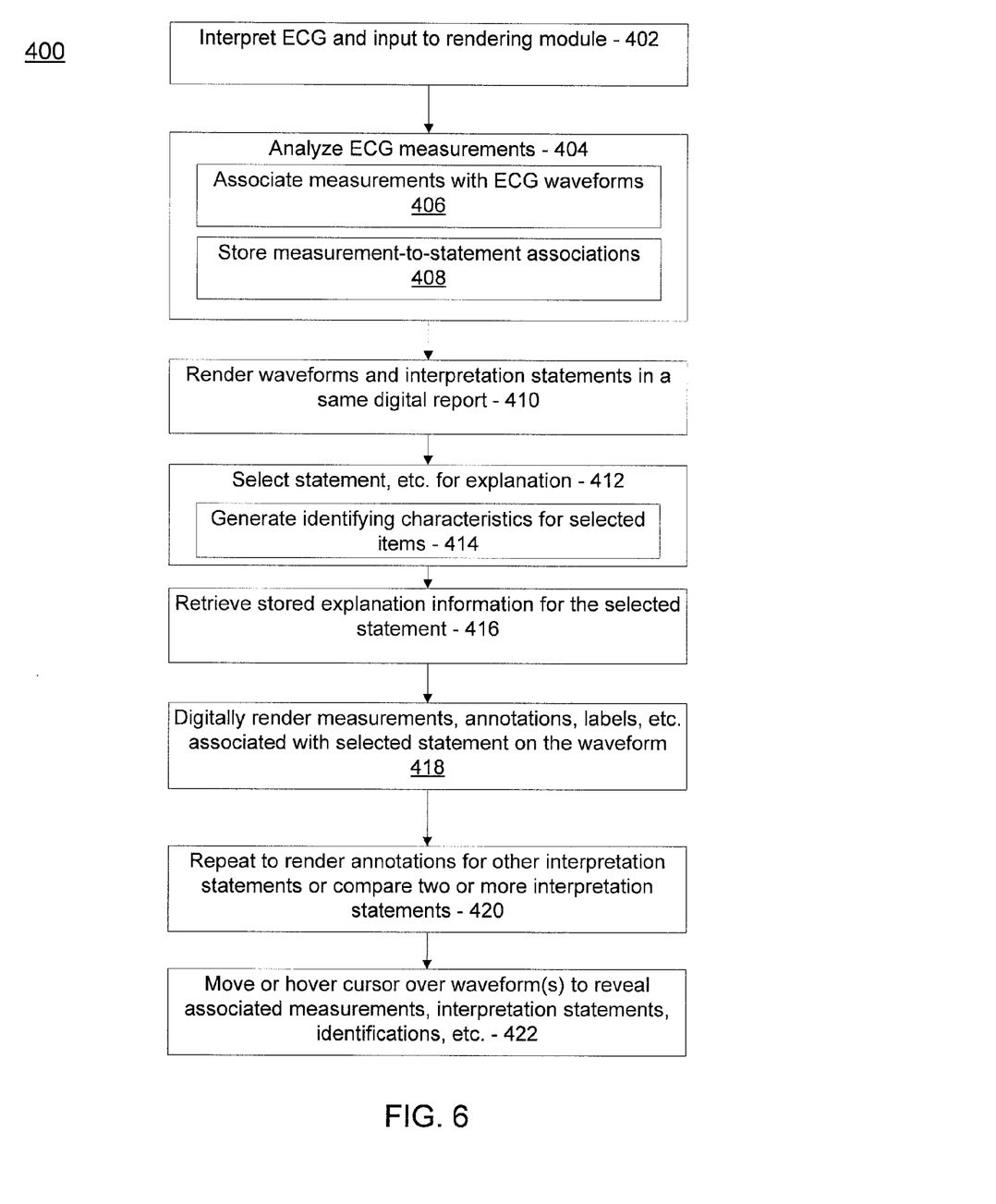
FIG. 6 is a block/flow diagram showing another system/method for producing and interpreting ECGs in accordance with one illustrative embodiment.

Referring to FIG. 6, another ECG rendering system/method 400 (e.g., module 152 of FIG. 1) is shown, which includes one or more modules that permit a user to view, analyze and edit an ECG report. In block 402, ECG waveforms are detected, measured and interpreted and then input to the rendering module. The ECG measurements may include, e.g., QRS duration, PR interval, QT interval, Q-wave amplitudes, R-wave amplitudes, S-wave amplitudes, Q-wave durations, R-wave durations, etc.

In block 404, the ECG is analyzed based on correspondence between interpretation and measurements. In block 406, interpretation statements based on a specific analysis for each detected abnormality are associated with their abnormal characteristics of the ECG waveforms. In block 408, the measurements used for the particular analysis are stored for each interpretation statement. The measurements may be stored with information including one or more of: a name, a value, a threshold, a categorical type, amplitude or duration (e.g., y direction or x direction measure), a reference to where the measurement and associated point, line, box or other shape should be marked on the waveform. This information and other information (e.g., user annotations) may be formatted for use as labels.

In block 410, the waveform is rendered or otherwise visualized in an ECG report. The report may include both interpretation statements and the waveforms. The interpretation statements are preferably provided in a same view as the waveform(s).

In block 412, a user selects a statement for explanation. This may be performed by, e.g., hovering over an interpretation statement with a cursor or pointing device or clicking on the statement. In block 414, identifying characteristics are indicated on selected items. In one embodiment, hovering over portions of the waveform may generate the appearance of previously stored labels, indicia, shapes, lines or permit identification of portions of the waveform or interpretation statement. In one example, the interpretation statement or other item may be highlighted, italicized, bolded, etc. so that the user knows which items has been selected.

In block 416, stored measurements and/or other information are retrieved for the selected interpretation statement. In block 418, the related measurements, annotations, labels, etc. referenced to the ECG waveform are digitally plotted or rendered to appear on the waveform. In block 418, for each measurement related to the selected statement, the measurement, label, annotation, etc. is plotted including lines, arrows, boxes, shapes, e.g., referenced to the isoelectric line and QRS onset. The line/box may be oriented horizontally or vertically based on whether it is an amplitude or a duration. The box may take other forms or shapes. The forms or shapes may include other features (color, texture, etc.) to represent other characteristics (e.g., a first point, a second point, etc.) of the measurements. A measurement label is also printed from the stored measurement name, the value, the threshold, etc.

In block 420, the process may be repeated for other statements in the interpretation statement list. It is preferable that each interpretation statement have its associated annotation appear only when the statement is selected; however, in accordance with other embodiments, a compare function may be provided so that two or more annotation sets are plotted together for multiple interpretation statements to further assist in understanding the ECG. In block 422, a cursor may be moved over a waveform by a user to reveal one or more of: a corresponding measurement value(s) that is/are related to that waveform, an abnormality associated with that portion of the waveform, identifying information for that portion of the waveform, a related textual interpretation that is associated with that abnormality or portion of the waveform, etc.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for diagnostic representation and interpretation of ECG leads on a digital display (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for electrocardiogram (ECG) interpretation, the system comprising:
a processor;
a memory coupled to the processor;
a rendering module stored in the memory and being configured to receive input from an ECG and correlate words describing a diagnosis with both an ECG measurement, made with respect to the ECG, and an abnormal portion of a waveform within the ECG that are consistent with the diagnosis;
a display device configured to display a rendering of the ECG, the words describing the diagnosis, and the ECG measurement that is consistent with the diagnosis;
an interface configured to permit user selection, within the display, of the diagnosis through a selection of the words describing the diagnosis, wherein
the display device is configured to project, onto the displayed rendering of the ECG and in response to the selection of the displayed words describing the diagnosis through the interface, visual indications of the ECG measurement and the abnormal portion of the waveform corresponding to the selected diagnosis.

2. The system as recited in claim 1, wherein the visual indications comprise a shape over the abnormal portion of the waveform corresponding to the selected diagnosis.

3. The system as recited in claim 1, wherein the visual indications comprise a label for the abnormal portion of the waveform corresponding to the selected diagnosis.

4. The system as recited in claim 1, wherein the visual indications comprise lines to indicate a measured distance with respect to the abnormal portion of the waveform corresponding to the selected diagnosis.

5. The system as recited in claim 1, wherein the visual indications include color differences, texture differences or shape differences.

6. The system as recited in claim 1, wherein the selected words describing the diagnosis are highlighted by a change in font, a change in color or a change in texture.

7. The system as recited in claim 1, wherein the system is included in an electrocardiograph, a defibrillator or a monitor.

8. The system as recited in claim 1, further comprising an ECG measurement module stored in the memory and being configured to receive digitized outputs to perform measurements on measurement data.

9. The system as recited in claim 8, further comprising a digitization module configured to provide the digitized outputs to the ECG measurement module.

10. A system for interpreting an electrocardiogram (ECG), the system comprising:
an interpretation module configured to interpret an ECG to provide words describing a diagnosis based on measurements of ECG waveforms made with respect to the ECG;
a rendering module configured in non-transitory storage media to associate the words describing the diagnosis with both an ECG measurement, made with respect to the ECG, and an abnormal portion of a waveform within the ECG that are consistent with the diagnosis;
a display device configured to display a rendering of the ECG, the words describing the diagnosis, and the ECG measurement that is consistent with the diagnosis; and
a selection device configured to select, within the display, the diagnosis through a selection of the words describing the diagnosis, wherein
the display device is configured to project, onto the displayed rendering of the ECG and in response to the selection of the displayed words describing the diagnosis, visual indications of the ECG measurement and the abnormal portion of the waveform corresponding to the selected diagnosis.

11. The system as recited in claim 10, wherein the visual indications comprise: (i) a shape over the abnormal portion of the waveform corresponding to the selected diagnosis or (ii) lines to indicate a measured distance with respect to the abnormal portion of the waveform corresponding to the selected diagnosis.

12. The system as recited in claim 10, wherein the visual indications comprise color differences, texture differences or shape differences.

13. The system as recited in claim 10, wherein the selected words describing the diagnosis are highlighted by a change in font, a change in color or a change in texture.

14. The system as recited in claim 10, wherein the system is included in an electrocardiograph, a defibrillator or a monitor.

15. The system as recited in claim 10, wherein:
the selection device includes a mouse, a trackball, a joystick or a touchpad, and
the selection is made by a point and click operation.

16. The system as recited in claim 10, wherein:
the selection device includes a touch screen for the display, and
the selection is made by touching the display with a finger or a stylus.

17. A method for interpreting an electrocardiogram (ECG), the method comprising:
interpreting an ECG to provide words describing a diagnosis based on measurements of ECG waveforms made with respect to the ECG;
associating the words describing the diagnosis with both an ECG measurement, made with respect to the ECG, and an abnormal portion of a waveform within the ECG that are consistent with the diagnosis;
displaying a rendering of the ECG, the words describing the diagnosis, and the ECG measurement that is consistent with the diagnosis;
selecting, within the display, the diagnosis through a selection of the words describing the diagnosis; and
projecting, onto the displayed rendering of the ECG and in response to the selection of the displayed words describing the diagnosis, visual indications of the ECG measurement and the abnormal portion of the waveform corresponding to the selected diagnosis.

18. The method as recited in claim 17, wherein:
the visual indications comprise a shape over the abnormal portion of the waveform corresponding to the selected diagnosis, and
the method further comprises generating the shape over the abnormal portion of the waveform to indicate positions for measured data contributing to the diagnosis.

19. The method as recited in claim 17, wherein:
the visual indications comprise lines to indicate a measured distance with respect to the abnormal portion of the waveform corresponding to the selected diagnosis, and
the method further comprises generating the lines and arrows to indicate information for measured data contributing to the diagnosis.

20. The method as recited in claim 17, wherein the visual indications comprise labels that include one or more of a name, a value, a threshold, a categorical type, an amplitude or a duration and a reference marked on the ECG waveform.

21. The method as recited in claim 17, further comprising selecting the words describing the diagnosis by a point and click operation or a touch screen operation.

22. The method as recited in claim 17, further comprising moving a cursor over a waveform to reveal corresponding measurement values, identification information or a related textual interpretation.

23. A non-transitory computer-readable storage medium storing machine readable instructions executable by a processor to operate a system for electrocardiogram (ECG) interpretation, the non-transitory computer readable medium comprising:
interpretation code for causing interpreting of an ECG to provide words describing a diagnosis based on measurements of ECG waveforms made with respect to the ECG;
association code for causing association of the words describing the diagnosis with both an ECG measurement, made with respect to the ECG, and an abnormal portion of a waveform within the ECG that are consistent with the diagnosis;
displaying code for causing display of a rendering of the ECG, the words describing the diagnosis, and the ECG measurement that is consistent with the diagnosis;
selection code for causing selection, within the display, the diagnosis through a selection of the words describing the diagnosis; and
rendering code for causing projection, onto the displayed rendering of the ECG and in response to the selection of the displayed words describing the diagnosis, visual indications of the ECG measurement and the abnormal portion of the waveform corresponding to the selected diagnosis.

24. The non-transitory computer-readable storage medium as recited in claim 23, wherein:
the visual indications comprise a shape over the abnormal portion of the waveform corresponding to the selected diagnosis, and
the medium further comprising generation code for causing generation of the shape to indicate positions for measured data contributing to the diagnosis.

25. The non-transitory computer-readable storage medium as recited in claim 23, wherein:
the visual indications comprise lines to indicate a measured distance with respect to the abnormal portion of the waveform corresponding to the selected diagnosis, and
the medium further comprising generation code for causing generation of the lines and arrows to indicate information for measured data contributing to the diagnosis.

26. The non-transitory computer-readable storage medium as recited in claim 23, wherein the visual indications comprise labels comprising one or more of a name, a value, a threshold, a categorical type, an amplitude or a duration and a reference marked on the ECG waveform.

27. The non-transitory computer-readable storage medium as recited in claim 23, wherein the selection code comprises highlighting code for causing the highlight of the words describing the diagnosis by a point and click operation or a touch screen operation.

* * * * *